(12) United States Patent
Gujraty et al.

(10) Patent No.: US 9,763,864 B2
(45) Date of Patent: Sep. 19, 2017

(54) COSMETIC COMPOSITIONS FOR HYDRATING SKIN

(71) Applicant: The Procter & Gamble Company, Cincinnati, OH (US)

(72) Inventors: Kunal Virendra Gujraty, Singapore (SG); Naohisa Yoshimi, Singapore (SG); Stevan David Jones, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/694,178

(22) Filed: Apr. 23, 2015

(65) Prior Publication Data
US 2015/0305998 A1 Oct. 29, 2015

Related U.S. Application Data

(60) Provisional application No. 61/982,884, filed on Apr. 23, 2014.

(51) Int. Cl.
| | | |
|---|---|---|
| *A61K 8/42* | (2006.01) | |
| *A61K 8/37* | (2006.01) | |
| *A61K 8/34* | (2006.01) | |
| *A61K 8/36* | (2006.01) | |
| *A61Q 19/00* | (2006.01) | |

(52) U.S. Cl.
CPC ............... *A61K 8/42* (2013.01); *A61K 8/345* (2013.01); *A61K 8/361* (2013.01); *A61K 8/37* (2013.01); *A61Q 19/00* (2013.01); *A61K 2800/592* (2013.01)

(58) Field of Classification Search
CPC .......... A61K 8/42; A61K 8/345; A61K 8/361; A61K 8/37
USPC ....................................................... 514/552
See application file for complete search history.

(56) References Cited

U.S. PATENT DOCUMENTS

| | | | |
|---|---|---|---|
| 4,389,418 A | 6/1983 | Burton | |
| 2006/0018858 A1* | 1/2006 | Chen | A61K 8/498 424/70.13 |
| 2006/0177397 A1 | 8/2006 | Candau | |
| 2006/0204467 A1 | 9/2006 | Littau | |
| 2012/0093751 A1 | 4/2012 | Nagano | |

FOREIGN PATENT DOCUMENTS

| | | | |
|---|---|---|---|
| DE | 10 2006 034529 A1 | 1/2008 | |
| DE | EP 2033617 A2 * | 3/2009 | ........... A61K 8/0212 |
| EP | 2 033 617 A2 | 10/2010 | |

OTHER PUBLICATIONS

EP 2033617—machine translation.*
International Search Report PCT/US2015/026738; Date of Mailing Aug. 24, 2015; 13 pages.
Database GNPD [Online] MINTEL; Aug. 31, 2011 (Aug. 31, 2011), "Sensitive skin Hydratouch Calming Day Cream", Database accession No. 160002.
Database GNPD [Online] MINTEL; Jan. 31, 2013 (Jan. 31, 2013). "Repairing Lotion", Database accession No. 1979652.
Database GNPD [Online] MINTEL; Feb. 28, 2014 (Feb. 28, 2014). "Hand and Nail Cream", Database accession No. 2311727.

* cited by examiner

*Primary Examiner* — Yevegeny Valenrod
(74) *Attorney, Agent, or Firm* — John G. Powell; S. Robert Chuey

(57) ABSTRACT

A cosmetic composition suitable for topical application is provided. The cosmetic composition comprises: a safe and effective amount of a humectant; a safe and effective amount of a lipid bilayer structurant, and a safe and effective amount of a chaotropic agent. The chaotropic agent denatures the cross-linked proteinaceous layer sitting immediately above skin thereby increasing the amount of humectant and lipid bilayer structurant that enters the stratum corneum; the humectant binds together with water molecules and the lipid bilayer structurant knits together the lipid bilayers of the stratum corneum thereby preventing water loss.

7 Claims, 1 Drawing Sheet

US 9,763,864 B2

COSMETIC COMPOSITIONS FOR HYDRATING SKIN

FIELD OF THE INVENTION

The present invention relates to skin care compositions that provide enhanced hydration while maintaining a good sensory experience during application. Specifically, a skin care composition is provided comprising a humectant, a chaotropic agent and a lipid bilayer structurant.

BACKGROUND OF THE INVENTION

Consumers have long desired hand, body and face lotions or creams which, when applied to the skin, improve the condition of the skin while simultaneously providing a pleasant tactile experience. In response to this, numerous cosmetic compositions have been formulated through the years to exhibit satisfactory spreading, feel, lubricity, and absorption upon application to the skin. More recently, consumers have been introduced to specialty lotions and creams formulated to treat dry skin conditions, known as "dry skin formulations".

A dry skin formulation described in U.S. Pat. No. 4,389,418 uses petrolatum or mineral oil as an occlusive emollient agent, and glycerin as a humectant. The occlusive emollient agent physically prevents or reduces moisture loss from the skin by formation of a water-impenetrable barrier over the stratum corneum and the humectant chemically attracts and holds water to the outside surface and upper layers of the stratum corneum, thereby increasing the overall water content in the skin itself. Other formulations currently on the market use increased amounts of glycerin to enhance the skin hydration properties.

While the above solutions may be effective in improving hydration of skin, they do not provide a good sensory feel upon application to skin—typically resulting in a sticky and tacky feel. Thus, there is a need to develop a composition that delivers an in vivo and consumer perceptible hydration benefit while not compromising the sensory feel of the composition during application.

SUMMARY OF THE INVENTION

A cosmetic composition suitable for topical application is provided. A cosmetic composition suitable for topical application, comprising: a safe and effective amount of a humectant; a safe and effective amount of a chaotropic agent; and a safe and effective amount of a lipid bilayer structurant.

A method of using a cosmetic composition is also provided. The method comprises applying a cosmetic composition to a facial skin surface in need of treatment, wherein the cosmetic composition comprises a safe and effective amount of humectant; a safe and effective amount of chaotropic agent; and a safe and effective amount of lipid bilayer structurant.

A method of enhancing skin hydration, the method comprising applying a topical composition to a skin surface, the composition comprising a safe and effective amount of humectant; a safe and effective amount of chaotropic agent; and a safe and effective amount of lipid bilayer structurant.

BRIEF DESCRIPTION OF THE DRAWINGS

While the specification concludes with claims, it is believed that the same will be better understood from the following description taken in conjunction with the accompanying drawings in which:

DETAILED DESCRIPTION OF THE INVENTION

Figure 1:
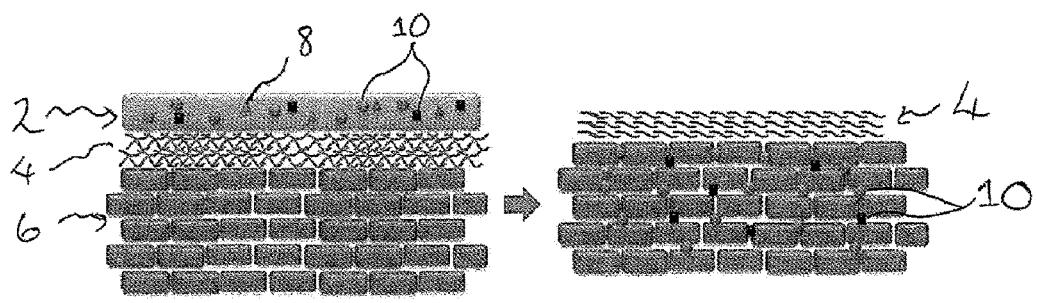
FIG. 1 is a schematic representation illustrating the effect of a chaotropic agent on skin penetration of humectants and barrier builders.
Figure 2:
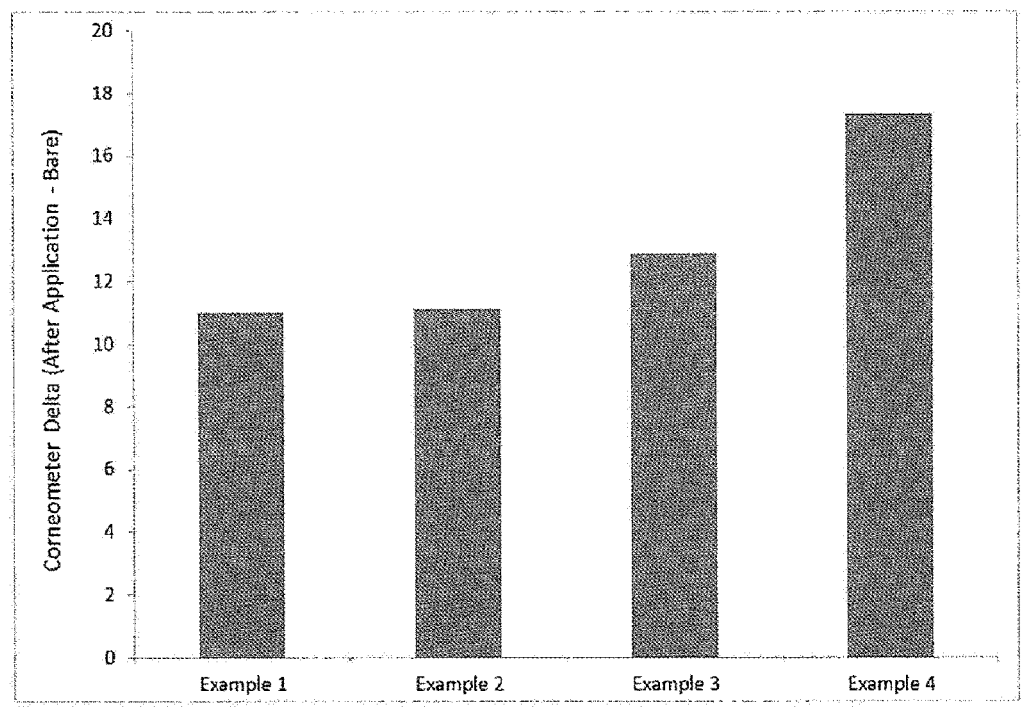
FIG. 2 shows in graphical format corneometer readings taken from forearm skin on which a cosmetic composition of the present invention has been applied.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Cosmetic composition" as used herein, means compositions suitable for topical application on mammalian keratinous tissue.

"Derivatives" as used herein, includes but is not limited to, amide, esther, ester, amino, carboxyl, acetyl, and/or alcohol derivatives of a given compound.

"Diluents" as used herein, refers to materials in which the humectant, chaotropic agent and lipid bilayer structurant can be dispersed, dissolved or otherwise incorporated.

"Safe and effective amount" means an amount sufficient to induce one or more biological effects, but low enough to avoid serious side effects, (e.g., undue toxicity or allergic reaction).

"Humectant" as used herein, means a substance which provides the skin with water-retention benefits.

"Keratinous tissue" as used herein, refers to keratin-containing layers disposed as the outermost protective covering of mammals which includes, but is not limited to, skin, hair, nails, cuticles, etc.

"Salts" as used herein, includes but is not limited to sodium, potassium, calcium, ammonium, manganese, copper, and/or magnesium salts of a given compound.

"Skin care actives" as used herein, means compounds that, when applied to the skin, provide a benefit or improvement to the skin. It is to be understood that skin care actives are useful not only for application to skin, but also to hair, nails and other mammalian keratinous tissue.

Skin care compositions commonly incorporate humectants to provide moisturisation and hydration benefits. For example, glycerin is typically found in skin care compositions, in combination with different skin care actives, to improve moisturisation. Recently, there has been a focus on improving various chronic skin benefits using different skin care compositions. However, very little attention has been given to providing more obvious in-use and acute moisturisation or hydration benefits and perceptions. One way to improve hydration in skin is to increase the amount of humectant in a skin care composition. While this is effective, increasing the humectant level tends to result in an unpleasant usage experience for the consumer as the resultant composition tends to be tacky or sticky upon application to skin. It has now surprisingly been discovered that combining a humectant with a chaotropic agent and a lipid bilayer structurant in a cosmetic composition provides a synergistic improvement in hydration of skin comparable with that resulting from an increase in humectant, but without the associated negative sensory side-effects.

Cosmetic Compositions

A cosmetic composition of the present invention may be applied to mammalian keratinous tissue, in particular to human skin. The cosmetic compositions may take various forms. For example, some non-limiting examples of forms include solutions, suspensions, lotions, creams, gels, toners, sticks, pencils, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

I. Humectants

Humectants have an affinity to hydrogen bonds of water molecules and to skin hydrophilic molecular functionalities, and accordingly bind themselves to internal water molecules as well as skin molecules. Topical application of cosmetic products containing humectants, (for example, glycerin) can be associated with improvements in barrier function, induction of biomarkers associated with keratinocyte proliferation and wound healing, reduction in melanin intensity, increases in epidermal thickness, and improvements in general skin appearance.

Non-limiting examples of suitable humectants for use in the present invention are described in W098/22085, W098/18444 and W097/01326 and include the following: amino acids and derivatives thereof such as proline and arginine aspartate, 1,3-butylene glycol, propylene glycol and water and codium tomentosum extract, collagen amino acids or peptides, creatinine, diglycerol, biosaccharide gum-1, glucamine salts, glucuronic acid salts, glutamic acid salts, polyethylene glycol ethers of glycerine (e. g. glycereth 20), glycerine, glycerol monopropoxylate, glycogen, hexylene glycol, honey, and extracts or derivatives thereof, hydrogenated starch hydrolysates, hydrolyzed mucopolysaccharides, inositol, keratin amino acids, LAREX A-200 (available from Larex), glycosaminoglycans, methoxy PEG 10, methyl gluceth-10 and-20 (both commercially available from Amerchol located in Edison, N.J.), methyl glucose, 3-methyl-1,3-butanediol, N-acetyl glucosamine salts, polyethylene glycol and derivatives thereof (such as PEG 15 butanediol, PEG 4, PEG 5 pentaerythitol, PEG 6, PEG 8, PEG 9), pentaerythitol, 1,2 pentanediol, PPG-1 glyceryl ether, PPG-9,2-pyrrolidone-5-carboxylic acid and its salts such as glyceryl pca, saccharide isomerate, SEACARE (available from Secma), sericin, silk amino acids, sodium acetylhyaluronate, sodium hyaluronate, sodium poly-aspartate, sodium polyglutamate, sorbeth 20, sorbeth 6, sugar and sugar alcools and derivatives thereof such as glucose, mannose and polyglycerol sorbitol, trehalose, triglycerol, trimethyolpropane, tris (hydroxymethyl) amino methane salts, and yeast extract, and mixtures thereof.

More preferably, the humectants for use herein are polyhydric alcohols selected from the group consisting of glycerin, diglycerin, glycerol, erythritol, arabitol, xylitol, ribitol, mannitol, sorbitol, galactitol, fucitol, maltitol, mannose, inositol, triethyleneglycol, sodium pyrrolidone carboxylic acid (PCA), zinc PCA and derivatives and mixtures thereof.

The composition contains a safe and effective amount of the humectant. In particular, it may contain from 1%, 2%, 3%, 4% or 5% to 8%, 10%, 20% or 30% by weight of a humectant. In embodiments, the composition may contain two or more different humectants, for example, the composition may contain glycerin and xylitol.

II. Chaotropic Agents

A chaotropic agent is a substance which disrupts the hydrogen-bonding network or structure of hydrogen-bond based macromolecules such as proteins and nucleic acids (e.g., DNA and RNA) and denatures the molecule by weakening the hydrophobic effect. Chaotropic solutes increase the entropy of a system by interfering with intramolecular interactions mediated by non-covalent forces such as hydrogen bonds, van der Waals forces, and hydrophobic effects. Chaotropic solutes decrease the net hydrophobic effect of hydrophobic regions (e.g., in lipid bilayers) because of a disordering of water molecules adjacent to the protein. This solubilises the hydrophobic region in the solution, thereby denaturing the protein. FIG. 1 illustrates schematically the effect that inclusion of a chaotropic agent 8 in a skin care composition 2 can have on skin. Specifically, it can be seen that the chaotropic agent denatures hydrogen bonds in the cross-linked proteinaceous layer 4 sitting above the stratum corneum lipid bilayers of skin allowing more of the composition (e.g., skin care active 10, humectant 10 etc) to partition into the surface layers 6 of the skin.

Examples of chaotropic agents that are known to disrupt the hydrophobic interactions and denature protein structure include, but are not limited to, guanidine hydrochloride ($R_1N-C(NR_2)-NR_3$), dimethyl sulfoxide (DMSO), urea (($R_1N-C(O)-NR_2$), and mixtures and derivates thereof, for example, hydroxyethyl urea. Upon topical application of a cosmetic composition containing chaotropic agents, the chaotropic agents drive transdermal penetration of molecules, including skin care actives, humectants and other ingredients, e.g. lipid bilayer structurants.

The composition contains a safe and effective amount of the chaotropic agent. Preferably, the composition may contain from about 0.5%, 1%, 1.5% or 2% to about 3%, 5%, 10% or 20% by weight of a chaotropic agent.

III. Lipid Bilayer Structurant

The main function of the epidermis is to act as the body's protective barrier, holding in vital water and keeping out pathogens. The epidermis itself is made of multiple layers, one of which is the stratum corneum. When the lipid bilayer structure is disrupted and becomes less organized, then its ability to effectively function as a barrier is negatively impacted.

It has been found that there are materials, known herein as lipid bilayer structurants, which will favorably interact with and pack the lipid bilayer allowing for improvement of its barrier function and leading to better skin hydration. The lipid bilayer structurant effectively knits together the lipid bilayer preventing movement (and loss) of water from the epidermis.

Examples of lipid bilayer structurants include, but are not limited to, batyl alcohol, glyceryl monooleate, isostearyl glyceryl ether, glyceryl isostearate, glyceryl monoerucate, glyceryl oleate, hexadecyl glyceryl ether, glyceryl monostearate, glyceryl monooleate, glyceryl monohydroxystearate, glyceryl monolinoleate, isopropyl isostearate, isopropoyl palmitate, myristyl myristate, myristyl palmitate, myristyl stearate, palmityl palmitate, cetyl stearate, stearyl stearate, isocetyl stearate, isooctadecyl palmitate, isohexadecyl isooctadecanoate, isooctadecanoic acid, 2-hydroxyoctadecyl ester, and cetyl glycol isostearate. In a preferred embodiment, the lipid bilayer structurant is isostearyl isostearate.

The composition comprises a safe and effective amount of the lipid bilayer structurant. For instance, the composition may contain from about 0.5%, 1%, 1.5% or 2% to 3%, 5%, 10% or 20% by weight of a lipid bilayer structurant. A minimum amount of lipid bilayer structurant is required to provide the synergistic benefit between inclusion of a humectant chaotropic agent and lipid bilayer structurant. However, if too much lipid bilayer structurant is included, it can inhibit initial penetration of skin care actives and humectant into skin and overall rate of penetration of skin care actives and humectants through the skin.

IV. Combination of Humectant, Chaotropic Agent and Lipid Bilayer Structurant

It has now surprisingly been found that combining one or more humectants with a lipid bilayer structurant and a chaotropic agent increases skin hydration levels. The present inventors have found that the chaotropic agent increases the amount of humectant and lipid bilayer structurant that enters the skin's surface layers, where the increased level of humectant increases the overall amount of water bound within the skin's surface layers, and the lipid bilayer structurant knits together lipid bilayers in the stratum corneum to reduce transdermal loss of water.

V. Other Ingredients

The cosmetic composition may include one or more skin care actives, for example Vitamin B3 actives such as niacinamide. The topical application of niacinamide may be associated with a variety of cosmetic skin care benefits. These may include: i) normalization of age associated depletions of nicotinamide coenzymes in skin, ii) up-regulation of epidermal ceramide synthesis with concurrent epidermal barrier benefits, iii) protection against damage produced by UV irradiation, iv) inhibition of the transfer of melanosomes from melanocytes to keratinocytes (thereby providing a potential skin tone benefit), and reduction in sebaceous lipogenesis. Thus in certain instances, it may be desirable to include niacinamide in the cosmetic composition in order to improve the appearance of aging/photodamaged skin.

The cosmetic compositions may also comprise a dermatologically acceptable carrier (which may also be referred to as a "carrier") within which the humectant, chaotropic agent and lipid bilayer structurant are incorporated to enable the compounds and optional other ingredients to be delivered to the skin. The carrier may contain one or more dermatologically acceptable solid, semi-solid or liquid fillers, diluents, solvents, extenders components, materials and the like. The carrier may be solid, semi-solid or liquid. The carrier may be provided in a wide variety of forms. Some non-limiting examples include simple solutions, (aqueous or oil based), emulsions, mousses (aerosol, non-aerosol), and solid forms (e.g., gels, sticks, flowable solids, amorphous materials).

The carriers may contain one or more dermatologically acceptable, hydrophilic diluents. Hydrophilic diluents include water, organic hydrophilic diluents such as lower monovalent alcohols (e.g., C1-C4) and low molecular weight glycols and polyols, including, but not limited to, propylene glycol, butylenes glycol, pentylene glycol, hexylene glycol, octylene glycol, polyethylene glycol (e.g., molecular weight 200-600 g/mole), polypropylene glycol (e.g., molecular weight 425-2025 g/mole), glycerol, butylene glycol, 1,2,4- butanetriol, sorbitol esters, 1,2,6-hexanetriol, ethanol, isopropanol, sorbitol esters, butanediol, ether propanol, ethoxylated ethers, propoxylated ethers and combinations thereof.

Carriers may also be in the form of an emulsion, such as oil-in-water emulsions, water-in-oil emulsions, and water-in-silicone emulsions. An emulsion may generally be classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. The aqueous phase may comprise water, such as a solution as described above. However, in other embodiments, the aqueous phase may comprise components other than water, including but not limited to water-soluble moisturizing agents, conditioning agents, antimicrobials, chelating agents, and/or other water-soluble skin care actives. Emulsions may also contain from about 1% to about 10% or from about 2% to about 5%, of an emulsifier, based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986).

A wide variety of optional components/ingredients may be included in the cosmetic compositions. For example, the cosmetic compositions may include absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in Harry's Cosmeticology, 7th Ed., Harry & Wilkinson (Hill Publishers, London 1982); in Pharmaceutical Dosage Forms-Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962-1965); and in The Handbook of Cosmetic Science and Technology, 1st Ed.. Knowlton & Pearce (Elsevier 1993).

Various cosmetic treatments may be employed. Skin surfaces of the most concern tend to be those not typically covered by clothing such as facial skin surfaces, hand and arm skin surfaces, foot and leg skin surfaces, and neck and chest skin surfaces, and scalp. In particular, facial and scalp skin surfaces, including the forehead, perioral, chin, periorbital, nose, and/or cheek skin surfaces, may be treated with the cosmetic compositions described herein.

The treatment method may include applying the cosmetic composition to a previously identified area of skin in need of treatment, or an area where one seeks to prevent, treat or reduce the appearance of age spots and/or improve skin tone evenness. Many regimens exist for the application of the cosmetic composition. The cosmetic composition may be applied at least once a day, twice a day, or on a more frequent daily basis, during a treatment period. When applied twice daily, the first and second applications are separated by at least 1 to 12 hours. Typically, the cosmetic composition may be applied in the morning and/or in the evening before bed. The treatment period is ideally of sufficient time to provide an improvement in the appearance of the age spots or skin tone evenness. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the cosmetic composition is applied at least once a day during a treatment period of at least 4 weeks, 8 weeks, or 12 weeks. In one embodiment the cosmetic composition is applied twice a day during a treatment period of at least 4 weeks, 8 weeks, or 12 weeks.

A method of using a cosmetic composition may comprise applying the cosmetic composition of the present invention to a facial skin surface in need of treatment. Furthermore, a method of enhancing skin hydration may comprise topically applying the cosmetic composition of the present invention to a skin surface.

EXAMPLES

The following examples are given solely for the purpose of illustration and are not to be construed as limiting the invention, as many variations thereof are possible. All measurements below are % by weight of the total composition.

| Ingredient Name | Example 1 | Example 2 | Example 3 | Example 4 |
| --- | --- | --- | --- | --- |
| Water | QS | QS | QS | QS |
| EDTA-2NA | 0.1 | 0.1 | 0.1 | 0.1 |
| Glycerin | 5 | 5 | 5 | 5 |
| Xylitol | 0 | 0 | 0 | 0 |
| Isostearyl Isostearate (ISIS) | 0 | 2 | 0 | 2 |
| Hydroxyethyl urea | 0 | 0 | 2 | 2 |
| Niacinamide | 5 | 5 | 5 | 5 |
| Sepiwhite | 0.2 | 0.2 | 0.2 | 0.2 |
| D- Panthenol | 0.5 | 0.5 | 0.5 | 0.5 |
| Lipidure PMB | 0.5 | 0.5 | 0.5 | 0.5 |
| Sodium Hyaluronate | 0.02 | 0.02 | 0.02 | 0.02 |
| Bisabolol | 0.1 | 0.1 | 0.1 | 0.1 |
| Oil | 10 | 10 | 10 | 10 |
| Emulsifier | 0.8 | 0.8 | 0.8 | 0.8 |
| Fatty Alcohol | 1.0 | 1.0 | 1.0 | 1.0 |
| Thickener | 0.62 | 0.62 | 0.62 | 0.62 |
| Preservative | 0.6 | 0.6 | 0.6 | 0.6 |
| Pigments/Powder | 3.78 | 3.78 | 3.78 | 3.78 |
| Amino Methyl Propanol | 0.08 | 0.08 | 0.08 | 0.08 |
| Benzyl Alcohol | 0.2 | 0.2 | 0.2 | 0.2 |
| Vitamin E acetate | 0.5 | 0.5 | 0.5 | 0.5 |
| Perfume | 0.03 | 0.03 | 0.03 | 0.03 |

All tests were conducted in controlled temperature controlled humidity condition (25 deg C.; Relative Humidity 50%) on forearm skin of males and females. The forearm test site was cleaned with tap water (with a pH of 6-9 and at ambient temperature) for 15 sec and dried using a tissue paper (gentle dabbing). After 20 minutes a baseline corneometer reading was taken, a known quantity (25 uL) of the sample composition was dispensed onto the test site (12 cm$^2$) and spread using finger cots. Corneometer readings (using Corneometer Model No. C825 commercialised by Courage+Kazaka®) were taken from five different locations from the test site of each panelist 10 minutes after application. An average of the five different corneometer readings of each panelist was calculated, as shown in the table of results below.

| | Change in Corneometer Reading vs. Baseline | | | |
| --- | --- | --- | --- | --- |
| Panelist umber | Example 1 | Example 2 | Example 3 | Example 4 |
| 1 | 26.3 | 11.74 | 17.64 | 28.8 |
| 2 | 22.24 | 4.56 | 16.36 | 18.7 |
| 3 | 5.72 | 2.64 | 13.9 | 13.6 |
| 4 | 9.48 | 10.96 | 9.6 | 9.5 |
| 5 | 12.82 | 17.72 | 3.78 | 14.2 |
| 6 | 11.94 | 10.6 | 9.84 | 13.8 |
| 7 | 14 | 23.32 | 23.42 | 29.2 |
| 8 | 17.12 | 18.96 | 23.62 | 21.3 |
| 9 | 1.34 | 10.36 | 8.76 | 18.3 |
| 10 | 6.1 | 8.56 | 7.96 | 9.8 |
| 11 | −1.66 | 6.26 | 16.94 | 18.6 |
| 12 | 8.9 | 11 | 13 | 21.8 |
| 13 | 13.08 | 9.32 | 7.3 | 9.1 |
| 14 | 10.16 | 7.22 | 6.66 | 9.7 |
| 15 | 7.68 | 13.74 | 14.64 | 23.9 |
| Average | 11.01 | 11.13 | 12.89 | 17.35 |
| Stdev | 7.27 | 5.51 | 5.95 | 6.74 |
| p-value | | 0.96 | 0.44 | 0.02 |

Each of examples 1 to 4 shown above contains a different combination of humectant, chaotropic agent and lipid bilayer structurant. Example 1 includes 5% glycerin; Example 2 includes 5% glycerin and 2% ISIS (lipid bilayer structurant); Example 3 includes 5% glycerin and 2% hydroxyethyl urea (chaotropic agent); and Example 4 includes 5% glycerin, 2% hydroxyethyl urea and 2% ISIS. Comparing Examples 2 and 3 with Example 1, it can be seen that there is an increase in epidermal hydration, as measured using a corneometer. By contrast, when looking at Example 4, it can be seen that there is a significant increase in epidermal hydration vs all other examples. It can further be seen that the increase in epidermal hydration of Example 4 compared with sample 1 is greater in magnitude than the sum of the increases of Examples 2 and 3 compared with Example 1. This shows an unexpected synergy when incorporating both a chaotropic agent and lipid bilayer structurant together with a humectant in a composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition suitable for topical application, comprising:
   i) 2% to 10% by weight of the total composition of a humectant;
   ii) 1% to 20% by weight of a lipid bilayer structurant; and
   iii) 1% to 20% by weight of a chaotropic agent which is selected from the group consisting of guanidine hydrochloride, amide, ether, ester, amino, carboxyl, acetyl, and alcohol derivatives of guanidine hydrochloride, and mixtures thereof.

2. The cosmetic composition of claim 1, wherein the humectant is a polyhydric alcohol, selected from the group consisting of glycerol, diglycerin, erythritol, arabitol, xylitol, ribitol, mannitol, sorbitol, galactitol, fucitol, maltitol, mannose, inositol, triethyleneglycol, sodium pyrrolidone carboxylic acid (PCA), zinc PCA, derivatives thereof, and mixtures thereof.

3. The cosmetic composition of claim 1, wherein the humectant is one or both of glycerin and xylitol.

4. The cosmetic composition of claim 1, wherein the lipid bilayer structurant is selected from the group consisting of batyl alcohol, glyceryl monooleate, isostearyl glyceryl ether, glyceryl isostearate, glyceryl monoerucate, glyceryl oleate, hexadecyl glyceryl ether, glyceryl monostearate, glyceryl monooleate, glyceryl monohydroxystearate, glyceryl monolinoleate, isopropyl isostearate, isopropoyl palmitate, myristyl myristate, myristyl palmitate, myristyl stearate, palmityl palmitate, cetyl stearate, stearyl stearate, isocetyl stearate, isooctadecyl palmitate, isohexadecyl isoctadecanoate, isooctadecanoic acid, 2-hydroxyoctadecyl ester, cetyl glycol isostearate, and mixtures thereof.

5. The cosmetic composition of claim 1, wherein the lipid bilayer structurant is isopropyl isostearate.

6. A method of using a cosmetic composition, comprising applying a cosmetic composition according to claim 1, to a facial skin surface in need of treatment.

7. A method of enhancing skin hydration, the method comprising applying a cosmetic composition according to claim 1, to a skin surface.

* * * * *